(12) United States Patent
Wang et al.

(10) Patent No.: US 11,578,096 B2
(45) Date of Patent: Feb. 14, 2023

(54) METHOD FOR PREPARING 7ALPHA-METHYL-19-ALDEHYDE-4-ANDROSTENE-3,17-DIONE BY ELECTROCATALYTIC OXIDATION

(71) Applicant: ZHEJIANG UNIVERSITY OF TECHNOLOGY, Zhejiang (CN)

(72) Inventors: Jianguo Wang, Zhejiang (CN); Suiqin Li, Zhejiang (CN); Xing Zhong, Zhejiang (CN); Jiahui He, Zhejiang (CN)

(73) Assignee: ZHEJIANG UNIVERSITY OF TECHNOLOGY, Zhejiang (CN)

( * ) Notice: Subject to any disclaimer, the term of this patent is extended or adjusted under 35 U.S.C. 154(b) by 0 days.

(21) Appl. No.: 17/539,213

(22) Filed: Dec. 1, 2021

(65) Prior Publication Data
US 2022/0204546 A1   Jun. 30, 2022

(30) Foreign Application Priority Data
Dec. 28, 2020   (CN) .......................... 202011577124.8

(51) Int. Cl.
*C07J 1/00* (2006.01)
(52) U.S. Cl.
CPC .................................. *C07J 1/0018* (2013.01)
(58) Field of Classification Search
CPC ....... C07J 1/0011; C07J 1/0018; C07J 1/0022
See application file for complete search history.

(56) References Cited

PUBLICATIONS

Rajeev et al., Review-Electrocatalytic Oxidation of Alcohols Using Chemically Modified Electrodes: A Review. J. Electrochem. Soc. 167, 136508 (Year: 2020).*

N.P. Van Vliet et al., "An alternative synthesis of 17β-hydroxy-7α-methyl-19-nor-17α-pregn-5(10)-en-20-yn-3-one (Org OD 14)," Recueil des Travaux Chimiques des Pays-Bas, Apr. 1986, pp. 111-115.
Gabriel Tojo et al., "Oxidation of Alcohols to Aldehydes and Ketones—A Guide to Current Common Practice," Springer Science & Business Media, Inc., Jun. 2006, pp. 1-388.
E.J.Corey et al., "Pyridinium chlorochromate. An efficient reagent for oxidation of primary and secondary alcohols to carbonyl compounds," Tetrahedron Letters, Jun. 1975, p. 2647.
Marie Jeanne Quirin et al., "Fonctionnalisation du δ-pyronène, un nouveau synthon terpénique," Canadian Journal of Chemistry, vol. 74, Oct. 1996, pp. 1852-1856, English abstract only.
Pan Gao-Feng et al., "mprovement of Synthesis of 7α-methyl-19-aldehyde-4-androstene-3,17-dione," Guangzhou Chemical Industry, vol. 38, 2010, pp. 1-3, English abstract only.

* cited by examiner

*Primary Examiner* — Barbara P Badio
(74) *Attorney, Agent, or Firm* — JCIPRNET

(57) ABSTRACT

The present invention relates to a method for preparing 7α-methyl-19-aldehyde-4-androstene-3,17-dione by electrocatalytic oxidation. The method specifically includes: adopting an H-shaped electrolytic cell for reaction, in an anode chamber, using a metal oxide catalyst as a working electrode, using 7α-methyl-17,19-dihydroxy-4-androstene-3-one as a reaction substrate, and dissolving it in a mixed solvent to be used as an anolyte, and adding nitroxide radicals to be used as a medium; and in a cathode chamber, using a platinum sheet as a counter electrode, using a weakly alkaline solution as a catholyte, carrying out an electrocatalytic oxidation reaction in a constant temperature water bath, adding an organic solvent at the end of the reaction for extraction to obtain an organic extract liquor, and taking an organic layer and carrying out distilling under a reduced pressure to obtain 7α-methyl-19-aldehyde-4-androstene-3,17-dione.

10 Claims, 1 Drawing Sheet

METHOD FOR PREPARING 7ALPHA-METHYL-19-ALDEHYDE-4-ANDROSTENE-3,17-DIONE BY ELECTROCATALYTIC OXIDATION

CROSS-REFERENCE TO RELATED APPLICATION

This application claims the priority benefit of China application serial no. 202011577124.8, filed on Dec. 28, 2020. The entirety of the above-mentioned patent application is hereby incorporated by reference herein and made a part of this specification.

FIELD OF TECHNOLOGY

The present invention relates to a method for synthesizing a steroid hormone drug product, belongs to the technical field of fine chemical production, in particular to a method for preparing 7α-methyl-19-aldehyde-4-androstene-3,17-dione by electrocatalytic oxidation.

BACKGROUND

7α-methyl-19-aldehyde-4-androstene-3,17-dione is a key intermediate for the synthesis of high-efficiency steroid hormones such as Mibolerone and Tibolone. Mibolerone and Tibolone products have progesterone, estrogen and androgen activities, and have significant effects in treating women's menopausal syndrome and preventing women's postmenopausal bone loss. In 1986, N. P. van Vleit et al. reported a method for oxidative synthesis of 7α-methyl-19-aldehyde-4-androstene-3,17-dione by using a Jones reagent as an oxidant, but the oxidant will peroxidize the 19-position hydroxy group to carboxylic acid during the reaction, which accounts for about 8% of the raw material. The yield reported in the literature for this step is only about 60%, and the yield needs to be improved (Redl. Trav. Chim. Pays-Bas, 1986, 105: 111-115). Therefore, looking for a mild and efficient oxidant is the only way to solve peroxidation. Over the years, many researchers have developed Collins reagents, pyridinium chlorochromate (PCC) reagents, pyridinium dichromate (PDC) reagents, etc., which have shown good activity and selectivity for the oxidation of alcohols (Springer Science+Business Media, Inc., 2006: 1-82; Tetrahedron Letters, 1975, 16(31): 2647-2650; Canadian Journal of Chemistry, 1996, 74: 1852-1856). In 2010, Gaofeng Pan et al. synthesized 7α-methyl-19-aldehyde-4-androstene-3,17-dione with 7α-methyl-17,19-dihydroxy-4-androstene-3-one as a raw material, dichloromethane as a solvent, and PCC as an oxidant, and explored the best reaction conditions for this reaction, which are as follows: the feed ratio of 7α-methyl-17,19-dihydroxy-4-androstene-3-one, the dichloromethane and the PCC oxidant is 20 g:250 mL:(60 to 65) g; and the reaction temperature is 23° C. to 27° C., the reaction time is 3 hours, and the mass yield is 85% (Guangzhou Chemical Industry, 2010, 38: 71-72, 79). However, the above preparation methods all use chemical oxidants, which have the problems of long reaction time, low product selectivity, environmental pollution, and the like. Looking for a more environmentally friendly green production technology has become a current research focus of fine chemical synthesis.

SUMMARY

The purpose of the present invention is to solve the above-mentioned problems in the prior art and to provide a method for preparing 7α-methyl-19-aldehyde-4-androstene-3,17-dione by electrocatalytic oxidation of 7α-methyl-17,19-dihydroxy-4-androstene-3-one, the technological process is green and environmentally friendly, the production technology is simple, the catalyst cost is low, the reaction efficiency is high, the yield is high, and the production cycle is short.

The method for preparing 7α-methyl-19-aldehyde-4-androstene-3,17-dione by electrocatalytic oxidation wherein the method comprises: with a reaction current controlled by a galvanostat, adopting an H-shaped electrolytic cell for reaction, wherein volumes of a cathode chamber and an anode chamber are both 20 mL to 100 mL, and the two electrode chambers are separated by an ion exchange membrane; in the anode chamber, using a metal oxide catalyst as a working electrode, using 7α-methyl-17,19-dihydroxy-4-androstene-3-one as a reaction substrate, and dissolving it in a mixed solvent to be used as an anolyte, and adding a certain amount of nitroxide radicals to be used as a medium; and in the cathode chamber, using a platinum sheet as a counter electrode, using a 0.1 mol/L to 1.0 mol/L weakly alkaline solution as a catholyte, carrying out an electrocatalytic oxidation reaction for 0.5 hours to 20 hours in a constant temperature water bath with a temperature of 20° C. to 60° C., a current of 50 mA to 1000 mA and a cell voltage of 1 V to 10 V, after the reaction is over and a reaction liquid is cooled, adding a suitable organic solvent for extraction to obtain an organic extract liquor, and taking an organic layer and carrying out distilling under a reduced pressure to obtain 7α-methyl-19-aldehyde-4-androstene-3,17-dione, and a reaction equation of which is as follows:

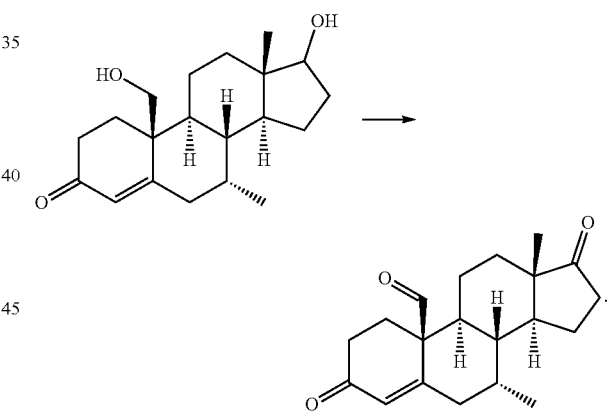

The method for preparing 7α-methyl-19-aldehyde-4-androstene-3,17-dione by electrocatalytic oxidation wherein volumes of the cathode chamber and the anode chamber are both 50 mL to 100 mL; and a concentration of the reactant raw material 7α-methyl-17,19-dihydroxy-4-androstene-3-one is 20 mmol/L to 100 mmol/L, preferably 50 mmol/L to 100 mmol/L.

The method for preparing 7α-methyl-19-aldehyde-4-androstene-3,17-dione by electrocatalytic oxidation wherein the anode mixed solvent is divided into a primary solvent and a secondary solvent, the primary solvent is a certain concentration of aqueous sodium carbonate solution with a concentration of 0.1 mol/L to 1.0 mol/L; and the secondary solvent is one of tetrahydrofuran, dichloromethane, acetonitrile and acetone.

The method for preparing 7α-methyl-19-aldehyde-4-androstene-3,17-dione by electrocatalytic oxidation wherein a feed volume ratio of the primary solvent and the secondary solvent in the mixed solvent is 7:3 to 5:5, and the pH of the mixed solvent is 9.0 to 12.0.

The method for preparing 7α-methyl-19-aldehyde-4-androstene-3,17-dione by electrocatalytic oxidation wherein the nitroxide radicals are 2,2,6,6-tetramethylpiperidine-N-oxide (TEMPO), 4-amino-TEMPO, 4-acetamido-TEMPO, and 4-hydroxy-TEMPO, and in an anode mixed solution, a concentration of the nitroxide radicals is 5 mmol/L to 20 mmol/L.

The method for preparing 7α-methyl-19-aldehyde-4-androstene-3,17-dione by electrocatalytic oxidation wherein the cathode weakly alkaline solution is a sodium carbonate solution, a sodium bicarbonate solution, a sodium phosphate solution or a sodium hydrogen phosphate solution, preferably the sodium carbonate solution with a concentration of 0.1 mol/L to 1.0 mol/L.

The method for preparing 7α-methyl-19-aldehyde-4-androstene-3,17-dione by electrocatalytic oxidation wherein when the electrocatalytic oxidation reaction is carried out, a current is 50 mA to 200 mA, a cell voltage is 2 V to 5 V, a reaction temperature is 30° C. to 60° C., and reaction time is 0.5 hours to 10 hours.

The method for preparing 7α-methyl-19-aldehyde-4-androstene-3,17-dione by electrocatalytic oxidation wherein the organic solvent used for extraction is toluene, dichloromethane, trichloromethane, ethyl acetate or chloroform.

The method for preparing 7α-methyl-19-aldehyde-4-androstene-3,17-dione by electrocatalytic oxidation wherein the metal oxide catalyst is composed of a carbon cloth carrier and a metal oxide supported on a carbon cloth, metals thereof are mainly iron, cobalt, nickel, and copper; and a supported capacity of the metal oxide on the carbon cloth is 2.0 mg/cm$^2$ to 2.5 mg/cm$^2$.

The method for preparing 7α-methyl-19-aldehyde-4-androstene-3,17-dione by electrocatalytic oxidation wherein a preparation method of the metal oxide catalyst comprises the following steps:

1) dissolving a metal salt in 40 mL to 80 mL of distilled water according to a feed ratio, then adding carbamide and ammonium fluoride, carrying out ultrasonic dispersion for 30 minutes to obtain a precursor solution A, wherein a metal iron salt raw material is ferric nitrate, ferric chloride, ferric oxide or ferroferric oxide; a cobalt salt raw material is cobalt nitrate, cobalt chloride, cobalt acetate or cobalt acetylacetonate; a metal nickel salt raw material is nickel nitrate, nickel chloride, nickel acetylacetonate or nickel acetate; and a metal copper salt raw material is copper nitrate, copper chloride, copper acetylacetonate or copper acetate;

2) adding the solution A in step 1) and the carbon cloth carrier into a hydrothermal reactor for a hydrothermal reaction for 5 hours to 12 hours at 80° C. to 160° C., after the reaction, cooling to a room temperature, taking out the carbon cloth carrier and then washing it three times with distilled water and ethanol, and then placing it in a 60° C. vacuum drying oven for drying to obtain a supported catalyst; and 3) placing the dried supported catalyst in step 2) in a tube furnace, calcining in an air-introduced atmosphere with a calcination temperature of 300° C. to 600° C. and a calcination time of 0.5 hours to 3 hours, and after the reaction is over, obtaining the metal oxide catalyst.

The method for preparing 7α-methyl-19-aldehyde-4-androstene-3,17-dione by electrocatalytic oxidation wherein:

in step 1), a concentration of a metal salt solution is 25 mmol/L to 50 mmol/L, a concentration of the carbamide is 100 mmol/L to 200 mmol/L, and a concentration of ammonium fluoride is 50 mmol/L to 100 mmol/L;

during the process in step 2), a hydrothermal temperature is 100° C. to 140° C., and a hydrothermal time is 6 hours to 12 hours; and in step 3), a calcination temperature is 400° C. to 600° C., and a calcination time is 1 hours to 2 hours.

By adopting the above technology, compared with an existing production technology of 7α-methyl-19-aldehyde-4-androstene-3,17-dione, the beneficial effects of the present invention are as follows:

1) the electrocatalytic oxidation reaction of the present invention uses electrons as oxidants, completely avoiding the use of a chromium oxidant and other oxidants, meeting environmental protection requirements while reducing costs;

2) compared with noble metal catalysts commonly used in the prior art, a cheap metal oxide catalyst used in the present invention has a low cost, avoiding consumption of rare noble metal raw materials, and improving its economic benefits;

3) in the technological method of the present invention, the electrocatalytic oxidation reaction process is carried out under normal temperature and pressure, and its reaction conditions are mild, which eliminates the safety risk in the industrial use of high temperature and high-pressure technological routes, and has the advantages of energy saving and emission reduction;

4) the present invention adjusts the selectivity of the whole reaction by controlling the reaction current and voltage. The present invention adopts constant current electrolysis, the conversion rate of the raw material 7α-methyl-17,19-dihydroxy-4-androsten-3-one is high, and the primary product 7α-methyl-19-aldehyde-4-androstene-3,17-dione has good selectivity and high product yield; and 5) the primary solvent (weakly alkaline reaction solution) and the secondary solvent used in the present invention can be reused, and no harmful gas and harmful waste liquid are generated during the production process. Therefore, the technology is non-toxic and harmless, and the entire technology is green and environmentally friendly and pollution-free.

DESCRIPTION OF THE EMBODIMENTS

The present invention will now be described in further detail in combination with the embodiments. The applications of the present invention are not limited to the following embodiments, and any formal modification made to the present invention will fall into the scope of protection of the present invention.

Figure 1:
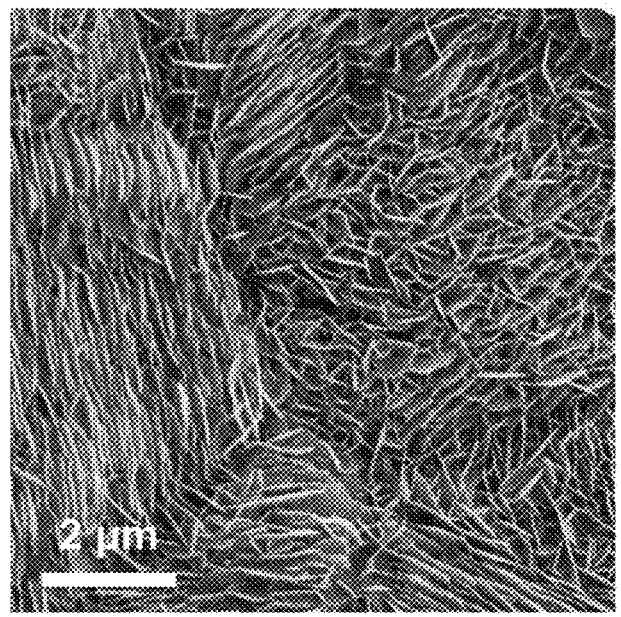
FIG. 1 is SEM image of an NiO/CF catalyst of Embodiment 1 at 2 μm.
Figure 2:
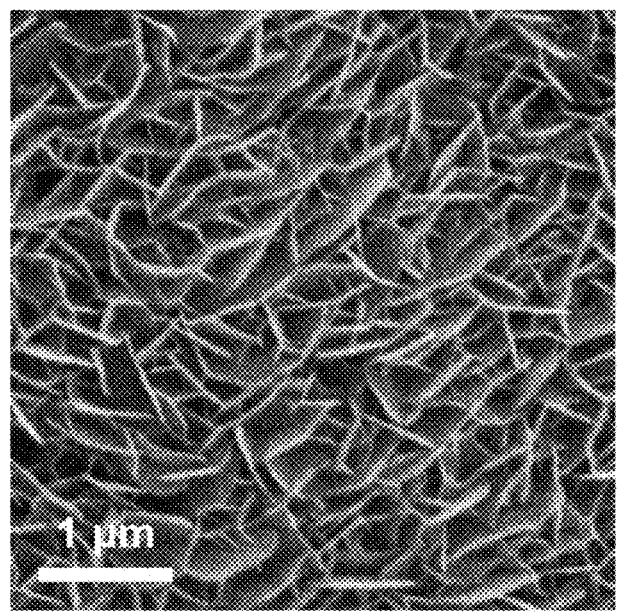
FIG. 2 is SEM image of an NiO/CF catalyst of Embodiment 1 at 1 μm.

Embodiment 1: Synthesis of NiO/CF Catalyst and Its Electrocatalytic Oxidation of 7α-methyl-17,19-dihydroxy-4-androstene-3-one to Prepare 7α-methyl-19-aldehyde-4-androstene-3,17-dione (1) 581 mg of nickel nitrate is taken and dissolved in 80 mL of distilled water according to a feed ratio, then 480 mg of carbamide and 296 mg of ammonium fluoride are added, and ultrasonic dispersion is carried out for 30 minutes to obtain a precursor solution A;

(2) the solution A in step 1) and a carbon cloth carrier are added into a hydrothermal reactor for a hydrothermal reaction for 12 hours at 120° C., after the reaction, cooling is carried out, and the carbon cloth carrier is taken out and then washed three times with distilled water and ethanol, and then placed in a 60° C. vacuum drying oven for drying to obtain a supported catalyst; and 3) the dried supported catalyst in step 2) is placed in a tube furnace, calcined for 2 hours at 600° C. in an air atmosphere, and cooled to a room temperature to obtain a supported nickel oxide catalyst, labeled as NiO/CF, and its SEM scanning electron micrographs are shown in FIGS. 1 and 2. From FIG. 1 and FIG. 2, it can be found that the NiO/CF catalyst has a nanoplate morphology, and the plate size is uniform.

The NiO/CF catalyst prepared in Embodiment 1 is used for electrocatalytic oxidation of 7α-methyl-17,19-dihydroxy-4-androstene-3-one to prepare 7α-methyl-19-aldehyde-4-androstene-3,17-dione, and the specific method is as follows:

The NiO/CF catalyst is directly used as a working electrode. A current is controlled by a galvanostat, an H-shaped electrolytic cell is adopted for reaction, an anode chamber and a cathode chamber have a volume of 100 mL and are separated by a cation exchange membrane, 60 mL of 1.0 mol/L aqueous sodium carbonate solution and 40 mL of an acetonitrile mixed solution (a feed volume ratio of a primary solvent and a secondary solvent is 6:4) are used as an electrolytic solution in the anode chamber, and 100 mL of 1.0 mol/L aqueous sodium carbonate solution is used as an electrolytic solution in the cathode chamber; in the anode chamber of the electrolytic cell, the prepared NiO/CF catalyst is used as the working electrode; and in the cathode chamber of the electrolytic cell, a platinum electrode is a counter electrode;

S1: 1.6 g of 7α-methyl-17,19-dihydroxy-4-androstene-3-one is taken as a reactant and added into the electrolytic solution in the anode chamber, and then 312 mg of 2,2,6,6-tetramethylpiperidine-N-oxide (TEMPO) is taken to be added into the electrolytic solution in the anode chamber;

S2: the whole electrolytic cell is placed in a constant temperature water bath to control a reaction system temperature to 30° C., stirring is carried out, a current is controlled to 200 mA, a voltage range is controlled to 2 V to 5 V, and a reaction time is 4 hours; and S3: after the electrolytic solution in the anode chamber in step S2 is cooled to a room temperature, it is extracted and layered by dichloromethane, and a dichloromethane phase is evaporated and separated to obtain a crude 7α-methyl-19-aldehyde-4-androstene-3,17-dione product, tracking is carried out by HPLC, and when the reaction reaches 4 hours, a raw material conversion rate is 98%, and selectivity of 7α-methyl-19-aldehyde-4-androstene-3,17-dione is 79%, the crude product is 1.48 g, and the yield is 93%.

Embodiment 2: Synthesis of CoO/CF Catalyst and Its Electrocatalytic Oxidation of 7α-methyl-17,19-dihydroxy-4-androstene-3-one to Prepare 7α-methyl-19-aldehyde-4-androstene-3,17-dione (1) 258 mg of cobalt chloride is taken and dissolved in 40 mL of distilled water according to a feed ratio, then 240 mg of carbamide and 74 mg of ammonium fluoride are added, and ultrasonic dispersion is carried out for 30 minutes to obtain a precursor solution A;

(2) the solution A in step 1) and a carbon cloth carrier are added into a hydrothermal reactor for a hydrothermal reaction for 10 hours at 100° C., after the reaction, cooling is carried out, and the carbon cloth carrier is taken out and then washed three times with distilled water and ethanol, and then placed in a 60° C. vacuum drying oven for drying to obtain a supported catalyst; and 3) the dried supported catalyst in step 2) is placed in a tube furnace, calcined for 2 hours at 400° C. in an air atmosphere, and cooled to a room temperature to obtain a supported cobalt oxide catalyst, labeled as CoO/CF.

The CoO/CF catalyst prepared in Embodiment 2 is used for electrocatalytic oxidation of 7α-methyl-17,19-dihydroxy-4-androstene-3-one to prepare 7α-methyl-19-aldehyde-4-androstene-3,17-dione, and the specific method is as follows:

The CoO/CF catalyst is directly used as a working electrode. A current is controlled by a galvanostat, an H-shaped electrolytic cell is adopted for reaction, an anode chamber and a cathode chamber have a volume of 50 mL and are separated by a cation exchange membrane, 25 mL of 0.5 mol/L aqueous sodium bicarbonate solution and 25 mL of an acetone mixed solution (a feed volume ratio of a primary solvent and a secondary solvent is 5:5) are used as an electrolytic solution in the anode chamber, and 50 mL of 0.5 mol/L aqueous sodium bicarbonate solution is used as an electrolytic solution in the cathode chamber; in the anode chamber of the electrolytic cell, the prepared CoO/CF catalyst is used as the working electrode; and in the cathode chamber of the electrolytic cell, a platinum electrode is a counter electrode;

S1: 0.8 g of 7α-methyl-17,19-dihydroxy-4-androstene-3-one is taken as a reactant and added into the electrolytic solution in the anode chamber, and then 210 mg of 4-amino-TEMPO is taken to be added into the electrolytic solution in the anode chamber;

S2: the whole electrolytic cell is placed in a constant temperature water bath to control a reaction system temperature to 50° C., stirring is carried out, a current is controlled to 100 mA, a voltage range is controlled to 3 V to 5 V, and a reaction time is 5 hours; and S3: after the electrolytic solution in the anode chamber in step S2 is cooled to a room temperature, it is extracted and layered by toluene, and a toluene phase is evaporated and separated to obtain a crude 7α-methyl-19-aldehyde-4-androstene-3,17-dione product, tracking is carried out by HPLC, and when the reaction reaches 5 hours, a raw material conversion rate is 92%, and selectivity of 7α-methyl-19-aldehyde-4-androstene-3,17-dione is 71%, the crude product is 0.68 g, and the yield is 85%.

Embodiment 3: Synthesis of $Fe_2O_3$/CF Catalyst and Its Electrocatalytic Oxidation of 7α-methyl-17,19-dihydroxy-4-androstene-3-one to Prepare 7α-methyl-19-aldehyde-4-androstene-3,17-dione (1) 726 mg of ferric nitrate is taken and dissolved in 60 mL of distilled water according to a feed ratio, then 720 mg of carbamide and 222 mg of ammonium fluoride are added, and ultrasonic dispersion is carried out for 30 minutes to obtain a precursor solution A;

(2) the solution A in step 1) and a carbon cloth carrier are added into a hydrothermal reactor for a hydrothermal reaction for 6 hours at 140° C., after the reaction, cooling is carried out, and the carbon cloth carrier is taken out and then washed three times with distilled water and ethanol, and then placed in a 60° C. vacuum drying oven for drying to obtain a supported catalyst; and 3) the dried supported catalyst in step 2) is placed in a tube furnace, calcined for 1 hour at 500° C. in an air atmosphere, and cooled to a room temperature to obtain a supported ferric oxide catalyst, labeled as $Fe_2O_3/CF$.

The $Fe_2O_3/CF$ catalyst prepared in Embodiment 3 is used for electrocatalytic oxidation of 7α-methyl-17,19-dihydroxy-4-androstene-3-one to prepare 7α-methyl-19-aldehyde-4-androstene-3,17-dione, and the specific method is as follows:

The $Fe_2O_3/CF$ catalyst is directly used as a working electrode. A current is controlled by a galvanostat, an H-shaped electrolytic cell is adopted for reaction, an anode chamber and a cathode chamber have a volume of 100 mL and are separated by a cation exchange membrane, 70 mL of 0.1 mol/L aqueous sodium carbonate solution and 30 mL of an acetonitrile mixed solution (a feed volume ratio of a primary solvent and a secondary solvent is 7:3) are used as an electrolytic solution in the anode chamber, and 100 mL of 0.1 mol/L aqueous sodium carbonate solution is used as an electrolytic solution in the cathode chamber; in the anode chamber of the electrolytic cell, the prepared $Fe_2O_3/CF$ catalyst is used as the working electrode; and in the cathode chamber of the electrolytic cell, a platinum electrode is a counter electrode;

S1: 3.2 g of 7α-methyl-17,19-dihydroxy-4-androstene-3-one is taken as a reactant and added into the electrolytic solution in the anode chamber, and then 312 mg of 4-acetamido-TEMPO is taken to be added into the electrolytic solution in the anode chamber;

S2: the whole electrolytic cell is placed in a constant temperature water bath to control a reaction system temperature to 40° C., stirring is carried out, a current is controlled to 200 mA, a voltage range is controlled to 2 V to 4 V, and reaction time is 8 hours; and S3: after the electrolytic solution in the anode chamber in step S2 is cooled to a room temperature, it is extracted and layered by ethyl acetate, and an ethyl acetate phase is evaporated and separated to obtain a crude 7α-methyl-19-aldehyde-4-androstene-3,17-dione product, tracking is carried out by HPLC, and when the reaction reaches 10 hours, a raw material conversion rate is 85%, and selectivity of 7α-methyl-19-aldehyde-4-androstene-3,17-dione is 64%, the crude product is 2.5 g, and the yield is 78%.

Embodiment 4: Synthesis of CuO/CF Catalyst and Its Electrocatalytic Oxidation of 7α-methyl-17,19-dihydroxy-4-androstene-3-one to Prepare 7α-methyl-19-aldehyde-4-androstene-3,17-dione (1) 400 mg of copper acetate is taken and dissolved in 50 mL of distilled water according to a feed ratio, then 450 mg of carbamide and 139 mg of ammonium fluoride are added, and ultrasonic dispersion is carried out for 30 minutes to obtain a precursor solution A;

(2) the solution A in step 1) and a carbon cloth carrier are added into a hydrothermal reactor for a hydrothermal reaction for 8 hours at 140° C., after the reaction, cooling is carried out, and the carbon cloth carrier is taken out and then washed three times with distilled water and ethanol, and then placed in a 60° C. vacuum drying oven for drying to obtain a supported catalyst; and 3) the dried supported catalyst in step 2) is placed in a tube furnace, calcined for 1 hour at 400° C. in an air atmosphere, and cooled to a room temperature to obtain a supported copper oxide catalyst, labeled as CuO/CF.

The CuO/CF catalyst prepared in Embodiment 4 is used for electrocatalytic oxidation of 7α-methyl-17,19-dihydroxy-4-androstene-3-one to prepare 7α-methyl-19-aldehyde-4-androstene-3,17-dione, and the specific method is as follows:

The CuO/CF catalyst is directly used as a working electrode. A current is controlled by a galvanostat, an H-shaped electrolytic cell is adopted for reaction, an anode chamber and a cathode chamber have a volume of 100 mL and are separated by a cation exchange membrane, 50 mL of 0.5 mol/L aqueous sodium carbonate solution and 50 mL of a tetrahydrofuran mixed solution (a feed volume ratio of a primary solvent and a secondary solvent is 5:5) are used as an electrolytic solution in the anode chamber, and 100 mL of 0.5 mol/L aqueous sodium carbonate solution is used as an electrolytic solution in the cathode chamber; in the anode chamber of the electrolytic cell, the prepared CuO/CF catalyst is used as the working electrode; and in the cathode chamber of the electrolytic cell, a platinum electrode is a counter electrode;

S1: 0.8 g of 7α-methyl-17,19-dihydroxy-4-androstene-3-one is taken as a reactant and added into the electrolytic solution in the anode chamber, and then 100 mg of 4-hydroxy-TEMPO is taken to be added into the electrolytic solution in the anode chamber;

S2: the whole electrolytic cell is placed in a constant temperature water bath to control a reaction system temperature to 30° C., stirring is carried out, a current is controlled to 50 mA, a voltage range is controlled to 3 V to 5 V, and a reaction time is 10 hours; and S3: after the electrolytic solution in the anode chamber in step S2 is cooled to a room temperature, it is extracted and layered by dichloromethane, and a dichloromethane phase is evaporated and separated to obtain a crude 7α-methyl-19-aldehyde-4-androstene-3,17-dione product, tracking is carried out by HPLC, and when the reaction reaches 10 hours, a raw material conversion rate is 89%, and selectivity of 7α-methyl-19-aldehyde-4-androstene-3,17-dione is 68%, the crude product is 0.7 g, and the yield is 87%.

Embodiment 5: CF Electrocatalytic Oxidation of 7α-methyl-17,19-dihydroxy-4-androstene-3-one to Prepare 7α-methyl-19-aldehyde-4-androstene-3,17-dione CF is directly used as a working electrode. A current is controlled by a galvanostat, an H-shaped electrolytic cell is adopted for reaction, an anode chamber and a cathode chamber have a volume of 50 mL and are separated by a cation exchange membrane, 30 mL of 1.0 mol/L aqueous sodium bicarbonate solution and 20 mL of an acetone mixed solution (a feed volume ratio of a primary solvent and a secondary solvent is 6:4) are used as an electrolytic solution in the anode chamber, and 50 mL of 1.0 mol/L aqueous sodium bicarbonate solution is used as an electrolytic solution in the cathode chamber; in the anode chamber of the electrolytic cell, the CF is directly used as the working electrode; and in the cathode chamber of the electrolytic cell, a platinum electrode is a counter electrode;

S1: 0.8 g of 7α-methyl-17,19-dihydroxy-4-androstene-3-one is taken as a reactant and added into the electrolytic solution in the anode chamber, and then 312 mg of 2,2,6,6-tetramethylpiperidine-N-oxide (TEMPO) is taken to be added into the electrolytic solution in the anode chamber;

S2: the whole electrolytic cell is placed in a constant temperature water bath to control a reaction system temperature to 60° C., stirring is carried out, a current is controlled to 50 mA, a voltage range is controlled to 3 V to 5 V, and a reaction time is 15 hours; and S3: after the electrolytic solution in the anode chamber in step S2 is cooled to a room temperature, it is extracted and layered by ethyl acetate, and an ethyl acetate phase is evaporated and separated to obtain a crude 7α-methyl-19-aldehyde-4-androstene-3,17-dione product, tracking is carried out by HPLC, and when the reaction reaches 15 hours, a raw material conversion rate is 72%, and selectivity of 7α-methyl-19-aldehyde-4-androstene-3,17-dione is 57%, the crude product is 0.5 g, and the yield is 63%.

For the reaction for electrocatalytic oxidation of 7α-methyl-17,19-dihydroxy-4-androstene-3-one to prepare 7α-methyl-19-aldehyde-4-androstene-3,17-dione, compared the five catalysts (NiO/CF, CoO/CF, Fe₂O₃/CF, CuO/CF, CF) prepared above, and results are shown in Table 1. Table 1 Table of Catalytic Effects of Catalysts in Embodiments 1-5

| Catalysts | Raw material conversion rate/% | Product selectivity/% | Yield/% |
| --- | --- | --- | --- |
| NiO/CF | 98% | 79% | 93% |
| CoO/CF | 92% | 71% | 85% |
| Fe₂O₃/CF | 85% | 64% | 78% |
| CuO/CF | 89% | 68% | 87% |
| CF | 72% | 57% | 63% |

From Table 1, it can be seen that compared with the CF catalyst, the metal oxide catalysts have improved raw material conversion rate, product selectivity and yield. The NiO/CF catalyst in Embodiment 1 of the present invention shows an excellent catalytic effect. When the reaction reaches 4 hours, the raw material conversion rate is 98%, the selectivity of 7α-methyl-19-aldehyde-4-androstene-3,17-dione is 79%, the crude product is 1.48 g, and the yield is 93%. Compared with other catalysts, the NiO/CF catalyst has good electrocatalytic activity. The reason may be that $Ni^{2+}$ firstly forms an $Ni^{3+}$ (NiOOH) intermediate state during the electrocatalytic oxidation process, which promotes the substrate 7α-methyl-17,19-dihydroxy-4-androstene-3-one to be easier to be adsorbed on the surface of the NiO/CF catalyst for the electrocatalytic oxidation reaction.

The above-mentioned embodiments are only a preferred solution of the present utility model, and do not impose any formal restriction on the present utility model. There are other variations and modifications on the premise of not exceeding the technical solution described in the claims.

What is claimed is:

1. A method for preparing 7α-methyl-19-aldehyde-4-androstene-3,17-dione by electrocatalytic oxidation, wherein the method comprises: with a reaction current and a voltage controlled by a galvanostat, adopting an H-shaped electrolytic cell for reaction, wherein volumes of a cathode chamber and an anode chamber are both 20 mL to 100 mL, and the two electrode chambers are separated by an ion exchange membrane; in the anode chamber, using a metal oxide catalyst as a working electrode, using 7a-methyl-17,19-dihydroxy-4- androstene-3-one as a reaction substrate, and dissolving it in a mixed solvent to be used as an anolyte, and adding a certain amount of nitroxide radicals to be used as a medium; and in the cathode chamber, using a platinum sheet as a counter electrode, using a 0.1 mol/L to 1.0 mol/L weakly alkaline solution as a catholyte, carrying out an electrocatalytic oxidation reaction for 0.5 hours to 20 hours in a constant temperature water bath with a temperature of 20° C. to 60° C., a current of 50 mA to 1000 mA and a cell voltage of 1 V to 10 V, after the reaction is over and a reaction liquid is cooled, adding an organic solvent for extraction to obtain an organic extract liquor, and taking an organic layer and carrying out distilling under a reduced pressure to obtain 7α-methyl-19-aldehyde-4-androstene-3,17-dione, and a reaction equation of which is as follows:

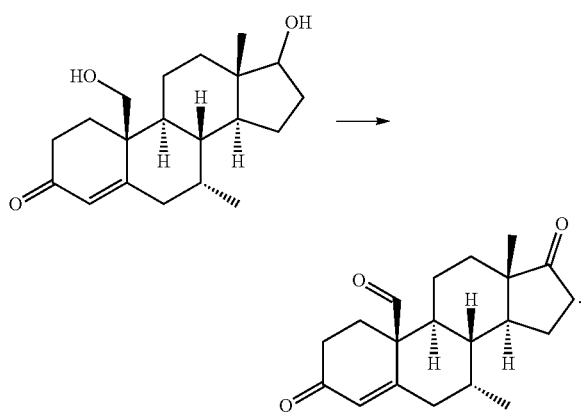

2. The method for preparing 7α-methyl-19-aldehyde-4-androstene-3,17-dione by electrocatalytic oxidation according to claim 1, wherein volumes of the cathode chamber and the anode chamber are both 50 mL to 100 mL; and a concentration of the reactant 7α-methyl-17,19-dihydroxy-4-androstene-3-one is 20 mmol/L to 100 mmol/L, 50 mmol/L to 100 mmol/L.

3. The method for preparing 7α-methyl-19-aldehyde-4-androstene-3,17-dione by electrocatalytic oxidation according to claim 1, wherein the mixed solvent in the anode chamber is divided into a primary solvent and a secondary solvent, the primary solvent is an aqueous sodium carbonate solution with a concentration of 0.1 mol/L to 1.0 mol/L; the secondary solvent is one of tetrahydrofuran, dichloromethane, acetonitrile and acetone; and a feed volume ratio of the primary solvent and the secondary solvent in the mixed solvent is 7:3 to 5:5, and the pH of the mixed solvent is 9.0 to 12.0.

4. The method for preparing 7α-methyl-19-aldehyde-4-androstene-3,17-dione by electrocatalytic oxidation according to claim 1, wherein the nitroxide radicals are TEMPO, 4-amino-TEMPO, 4-acetamido-TEMPO or 4-hydroxy-TEMPO, and in an anode mixed solution, a concentration of the nitroxide radicals is 5 mmol/L to 20 mmol/L.

5. The method for preparing 7α-methyl-19-aldehyde-4-androstene-3,17-dione by electrocatalytic oxidation according to claim 1, wherein in the cathode chamber, the weakly alkaline solution is a sodium carbonate solution, a sodium bicarbonate solution, a sodium phosphate solution or a sodium hydrogen phosphate solution, preferably the sodium carbonate solution with a concentration of 0.1 mol/L to 1.0 mol/L.

6. The method for preparing 7α-methyl-19-aldehyde-4-androstene-3,17-dione by electrocatalytic oxidation according to claim 1, wherein when the electrocatalytic oxidation reaction is carried out, a current is 50 mA to 200 mA, a cell voltage is 2 V to 5 V, a reaction temperature is 30° C. to 60° C., and reaction time is 0.5 hours to 10 hours.

7. The method for preparing 7α-methyl-19-aldehyde-4-androstene-3,17-dione by electrocatalytic oxidation according to claim 1, wherein the organic solvent used for extraction is toluene, dichloromethane, trichloromethane, ethyl acetate or chloroform.

8. The method for preparing 7α-methyl-19-aldehyde-4-androstene-3,17-dione by electrocatalytic oxidation according to claim 1, wherein the metal oxide catalyst is composed of a carbon cloth carrier and a metal oxide supported on a carbon cloth, metals thereof are iron, cobalt, nickel, and copper; and a supported capacity of the metal oxide on the carbon cloth is 2.0 mg/cm$^2$ to 2.5 mg/cm$^2$.

9. The method for preparing 7α-methyl-19-aldehyde-4-androstene-3,17-dione by electrocatalytic oxidation according to claim 8, wherein a preparation method of the metal oxide catalyst comprises the following steps:

1) dissolving a metal salt in 40 mL to 80 mL of distilled water according to a feed ratio, then adding carbamide and ammonium fluoride, carrying out ultrasonic dispersion to obtain a precursor solution A, wherein metals in the metal salt are iron, cobalt, nickel, and copper; an iron salt is ferric nitrate, ferric chloride, ferric oxide or ferroferric oxide; a cobalt salt raw material is cobalt nitrate, cobalt chloride, cobalt acetate or cobalt acetylacetonate; a nickel salt raw material is nickel nitrate, nickel chloride, nickel acetylacetonate or nickel acetate; and a copper salt raw material is copper nitrate, copper chloride, copper acetylacetonate or copper acetate;

2) adding the solution A in step 1) and the carbon cloth carrier into a hydrothermal reactor for a hydrothermal reaction for 5 hours to 12 hours at 80° C. to 160° C., after the reaction, cooling to a room temperature, taking out the carbon cloth carrier and then washing it three times with distilled water and ethanol, and then placing it in a 60° C. vacuum drying oven for drying to obtain a supported catalyst; and 3) placing the dried supported catalyst in step 2) in a tube furnace, calcining in an air-introduced atmosphere with a calcination temperature of 300° C. to 600° C. and a calcination time of 0.5 hours to 3 hours, and after the reaction is over, obtaining the metal oxide catalyst.

10. The method for preparing 7α-methyl-19-alaldehyde-4-androstene-3,17-dione by electrocatalytic oxidation according to claim 9, wherein:

in step 1), a concentration of a metal salt solution is 25 mmol/L to 50 mmol/L, a concentration of the carbamide is 100 mmol/L to 200 mmol/L, and a concentration of ammonium fluoride is 50 mmol/L to 100 mmol/L;

during the process in step 2), a hydrothermal temperature is 100° C. to 140° C., and a hydrothermal time is 6 hours to 12 hours; and in step 3), a calcination temperature is 400° C. to 600° C., and a calcination time is 1 hours to 2 hours.

* * * * *